United States Patent [19]
Witt

[11] Patent Number: 5,136,252
[45] Date of Patent: Aug. 4, 1992

[54] APPARATUS AND METHODS FOR EVALUATING RESISTIVE BODIES

[75] Inventor: George C. Witt, Township of Hillsborough, Somerset County, N.J.

[73] Assignee: AT&T Bell Laboratories, Murray Hill, N.J.

[21] Appl. No.: 628,272

[22] Filed: Dec. 17, 1990

[51] Int. Cl.$^5$ ............................................. G01R 27/26
[52] U.S. Cl. ................................... 324/715; 324/718; 324/724
[58] Field of Search ............... 324/715, 722, 713, 724, 324/718

[56] References Cited

U.S. PATENT DOCUMENTS

| | | | |
|---|---|---|---|
| 3,303,418 | 2/1967 | Rose | 324/715 |
| 3,611,125 | 10/1971 | Sharon et al. | 324/715 |
| 3,995,213 | 11/1976 | Robinson et al. | 324/715 |
| 4,446,424 | 4/1984 | Chatanier et al. | 324/713 |
| 4,667,149 | 5/1987 | Cohen et al. | 324/715 |

FOREIGN PATENT DOCUMENTS 0345473  12/1989  European Pat. Off. ............ 324/713

OTHER PUBLICATIONS

"Resistivity Measurements Make a Useful QC Tool", by W. R. Hain, *Metal Progress*, (Apr. 1986) pp. 27–29.
"The Measurement of Crack Depths By The Direct-Current Conduction Method", by J. G. Buchanan & R. C. A. Thurston, *Non-Destructive Testing*, Sep.–Oct. 1956, pp. 36–39.
"The Potentials of Infinite Systems of Sources & Numerical Solutions of Problems in Semiconductor Engineering", by A. Uhlir, Jr., *Bell System Technical Journal*, vol. 34, Jan. 1955. pp. 105–128.
"Measurement of Sheet Resistivities with the Four-Point Probe", by F. M. Smits, *Bell System Technical Journal*, vol. 37, No. 3 May 1958. pp. 711–718.
"Resistivity Testing for Quality Control", *Materials Evaluation*, Aug. 1986, pp. 1066–1074.

*Primary Examiner*—Kenneth A. Wieder
*Assistant Examiner*—Maura K. Regan
*Attorney, Agent, or Firm*—Ruloff F. Kip, Jr.

[57] ABSTRACT

A probe holder mounts a pair of spaced current probes, a pair of spaced primary voltage probes inward of such current probes and a pair of spaced secondary voltage probes outward of such current probes. Each of the secondary voltage probes and the nearer thereto of the primary voltage probes is on the same equipotential contour calculated by assuming that the current probes contact and pass current through a planar homogeneously resistive sheet with infinite boundaries and of infinitesimal thickness. Electroconductive bodies are evaluated for resistive anomalies therein by contacting the body of all the probes and passing current through the body between the current probes. The voltages $V_a$, $V_b$ and $V'_a$, $V'_b$ responsively sensed on the surface of such body by, respectively, such two primary probes and such two secondary probes are used to derive first and second signals as functions of the voltage differentials $V_a - V_b$ and $V'_a - V'_b$ respectively. From those signals there is derived a third signal as a function of $(V'_a - V'_b) - (V_a - V_b)$ which is fed to output means to provide an output comprising information about such body. The third signal may additionally be a function of the set value of a bias signal. The output is suppressed by one or more validity checking circuits when a limit is exceeded by one or more of the voltages in the group consisting of the sensed voltages and the voltage differentials. The system may be adapted to operate substantially as described above when one of the four voltage probes is eliminated.

28 Claims, 7 Drawing Sheets

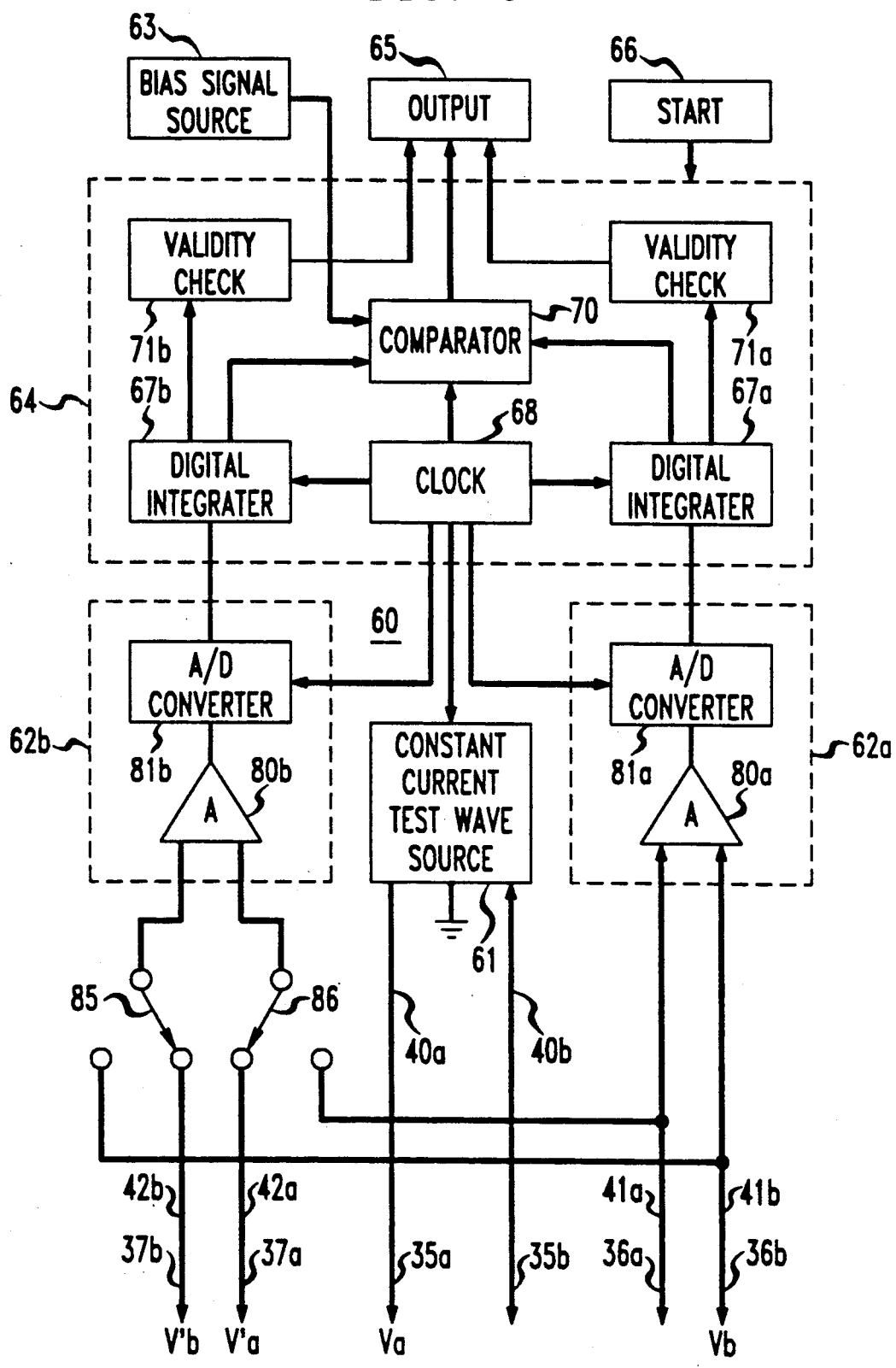

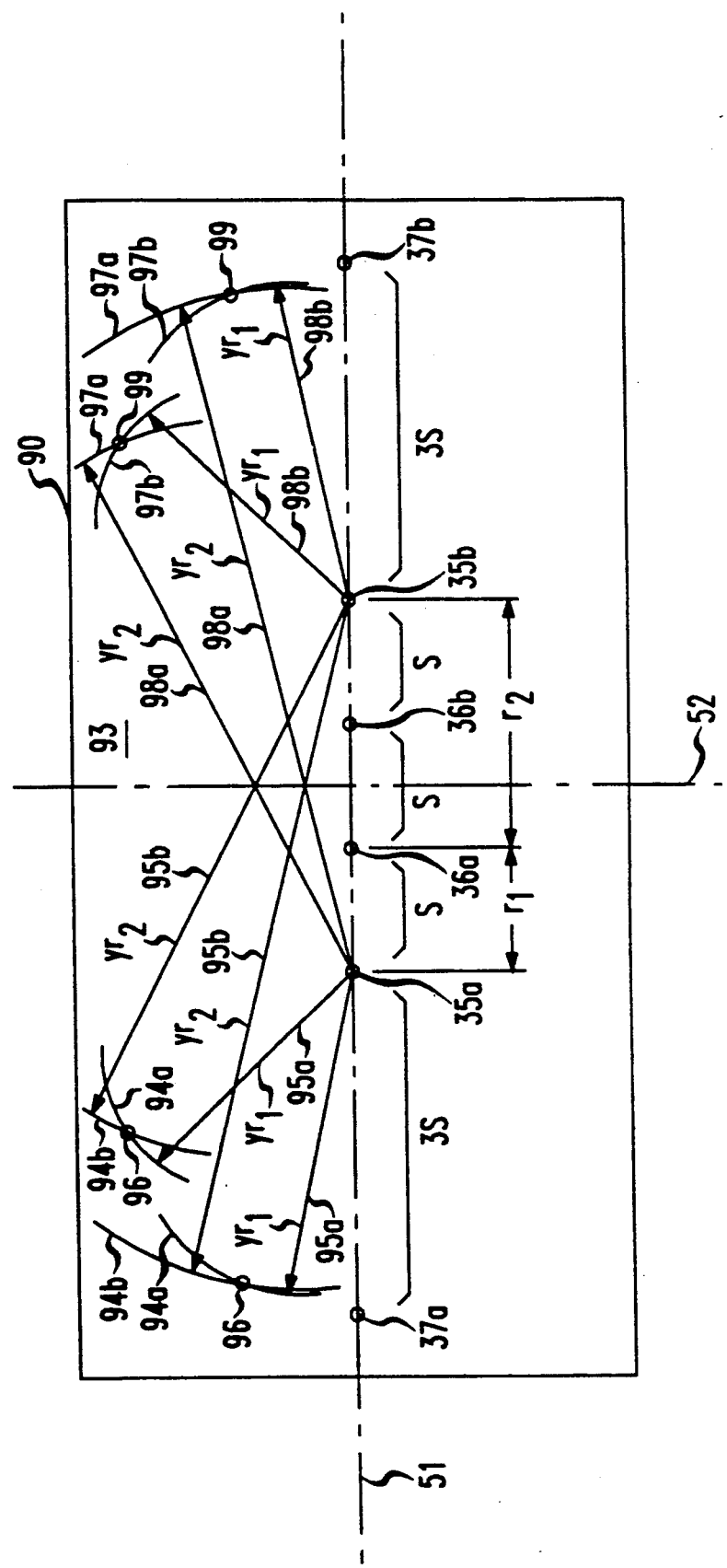

APPARATUS AND METHODS FOR EVALUATING RESISTIVE BODIES

FIELD OF THE INVENTION

This invention relates generally to apparatus and methods for testing for resistivity conditions in electroconductive bodies and, more particularly, to apparatus and methods of such kind for use with mechanical parts, structural assemblages or other products to provide indications of defects therein (or other of their features) affecting the apparent resistivities of part(s) or all of such items.

BACKGROUND OF THE INVENTION

In an article entitled "Resistivity Testing for Quality Control," appearing on pages 1066-1074 of the August 1986 issue of the publication *Materials Evaluation*, (the "Materials Evaluation" article) and incorporated herein by reference and made a part hereof, there is disclosed apparatus adapted by testing for resistivity conditions in machine parts to provide indications of defects or other features of such parts. That apparatus comprises a probe mounting head, a pair of outer current probes mounted by and projecting forward from said head and spaced apart by a gap, a pair of similarly mounted and projecting inner voltage probes disposed in said gap between said current probes, a current source connected to said current probes for supplying them with current of predetermined value, and indicating means connected to such voltage probes for sensing, measuring and indicating voltages developed between them.

In operating the apparatus, the head is brought to a mechanical part to be tested to produce contact between that part and all four probes. Current of predetermined character and value is then caused to flow through the part between the current probes in contact therewith to produce between the voltage probes a voltage of a value which, in accordance with the classic equation in electricity, $V=IR$, varies directly with such current as multipled by a quantity $\rho_a$ denoted the apparent resistivity of the region of the part explored by the current flow therethrough. It follows that if the effective value of the current can be treated as a constant, the voltage measured between the voltage probes will be in direct proportion with the value of $\rho_a$.

The value of $\rho_a$ is, in itself, however, a function of at least three parameters as they exist in such region, namely the composition of the material of the part and the resulting bulk resistivity of such material, the configuration of the part (e.g., its thickness, nearness of edges to the probes, etc.) and the degree of presence of structural defects (e.g., cracks, voids, dislocations) in the part. Assuming however that, in testing a series of parts, the first two factors of composition and configuration can be relied upon as not varying enough from part to part to produce effects in the total value of the measured voltage which would tend to mask changes caused in such value by a defect or defect sought to be detected, then the apparatus can be used to screen out all parts in such series which have such defects to an unacceptable degree. That is, the apparatus can be calibrated by applying the probes to a part known to be acceptably free of defects, noting the value then obtained of the voltage produced between the two voltage probes, and utilizing such value as a standard value with which are compared the voltage values obtained from probing the other parts. The ones of such parts yielding measured voltages which deviate little enough from the standard value to fall within a predetermined range of acceptability are parts which will be kept. Parts which do not meet that criteria will be rejected.

Instead of using the four-probe technique to screen part(s) or all of machine parts, structural assemblages or the like for structural defects, such technique may be employed to provide a measure of the degree of presence in such items of some other feature of interest. For example, the depth of case hardening of drive shafts will, by virtue of changing the composition and, hence, bulk resistivity of the shaft material through which current flows in using such technique, produce commensurate changes in the total voltage generated between the voltage probes by such flow in the course of such use. Hence, if it can reasonably be assumed that the effects on such total voltage of variations therein caused by variations in the configuration of or by defects in the drive shafts being inspected are effects which can be ignored as insignificant, then such variations in such total voltage can be utilized to provide a useful measure of such depth of case hardening.

Such four-probe technique for evaluating electroconductive bodies has, however, the problem that such masking effects can occur with undesirable frequency in the practical application of such technique. Another problem which can arise in such application is that, even though the contributions to the total measured voltage derived from variations in the factors affecting such voltage but irrelevant to the feature sought to be measured can be small enough so as to not mask out the contribution to such voltage caused by the presence or absence of, or variations in, such feature, nevertheless, such contributions from such irrelevant parameters can be large enough as to make the selection of a particular range of deviation from such standard value of voltages obtained by such technique from inspected parts an undesirably imprecise "yardstick" of which of such parts really ought to be accepted and which should not.

SUMMARY OF THE INVENTION

These and other problems are reduced or obviated according to the invention by providing apparatus comprising a pair of spaced current probes adapted to contact the exterior surface of an electroconductive body and to pass therethrough a flow of current productive on such surface of two sets of equipotential contours respectively corresponding to such two current probes, the contours of each set being closed curves each surrounding the point of contact on such surface of the corresponding current probe, at least three voltage probes adapted to contact said surface at respective locations spaced from each other and from said current probes, the points of contact with such surface of two of such voltage probes being located on two of said contours respective to such two voltage probes, and the point of contact with such surface of the third of such voltage probes being disposed substantially at a position on one of such two contours which is substantially displaced around that contour from the position thereon of that one of such two probes which is respective to that contour, signal generating means electrically coupled to such three voltage probes and responsive to said current flow and consequent voltages sensed by said voltage probes to produce two signals representative of two substantially non-zero voltage differentials existing among such three voltage probes, signal-combining means responsive to such two signals to derive from them a resultant signal as a function of such two voltage differentials, and means responsive to said resultant signal to provide an output representative of a resistivity-affected condition of such body. By properly selecting such two voltage differential signals and the manner in which they are combined to yield the mentioned resultant signal, it is possible to wire a less offset against each other the respective contributions to the values of the two voltage differential signals of factors present in such body which are extraneous to the feature of the body about which information is being sought by its testing by the apparatus so as, by such offsetting, to yield a resultant signal more sensitive to such feature (i.e., more informative about it) than could be obtained by the prior art four-probe technique.

BRIEF DESCRIPTION OF THE DRAWINGS

For a better understanding of the invention, reference is made to the following description of an exemplary embodiment thereof and to the accompanying drawings wherein:

FIG. 2 is a block diagram of the apparatus just referred to with the probe holder being shown schematically;

FIG. 7 is a representation of a mathematical method of constructing equipotential contours on the FIG. 6 sheet;

In the description which follows, elements designated by the same reference numerals with different alphabetical suffixes are counterparts of each other, and the description of any one such element shall, unless the context otherwise requires, be taken to apply equally to its counterpart.

DETAILED DESCRIPTION OF EMBODIMENT

Figure 1:
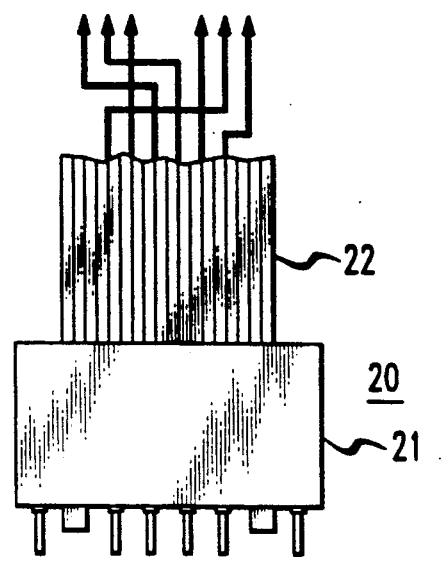
FIG. 1 is an isometric view of the structure of a probe holder constituting part of apparatus representative of the invention.

Referring to FIG. 1, the reference numeral 20 designates a probe holder which comprises a probe mounting head 21, and which may also comprise a hollow arm 22 shown broken away in FIG. 1. Head 21 is fixedly attached to the front of the arm. Arm 22 may be part of a testing machine (not shown) adapted under computer control to move head 21 vertically towards and away from a resistive article which has been positioned beneath the head to be tested by it.

Signals produced in the course of such testing are developed on the shown leads extending upward through arm 22 to circuits by which such signals are processed to yield an output which is a measure of a resistive condition of such article, and which provides information about a feature or features thereof.

Figure 4:
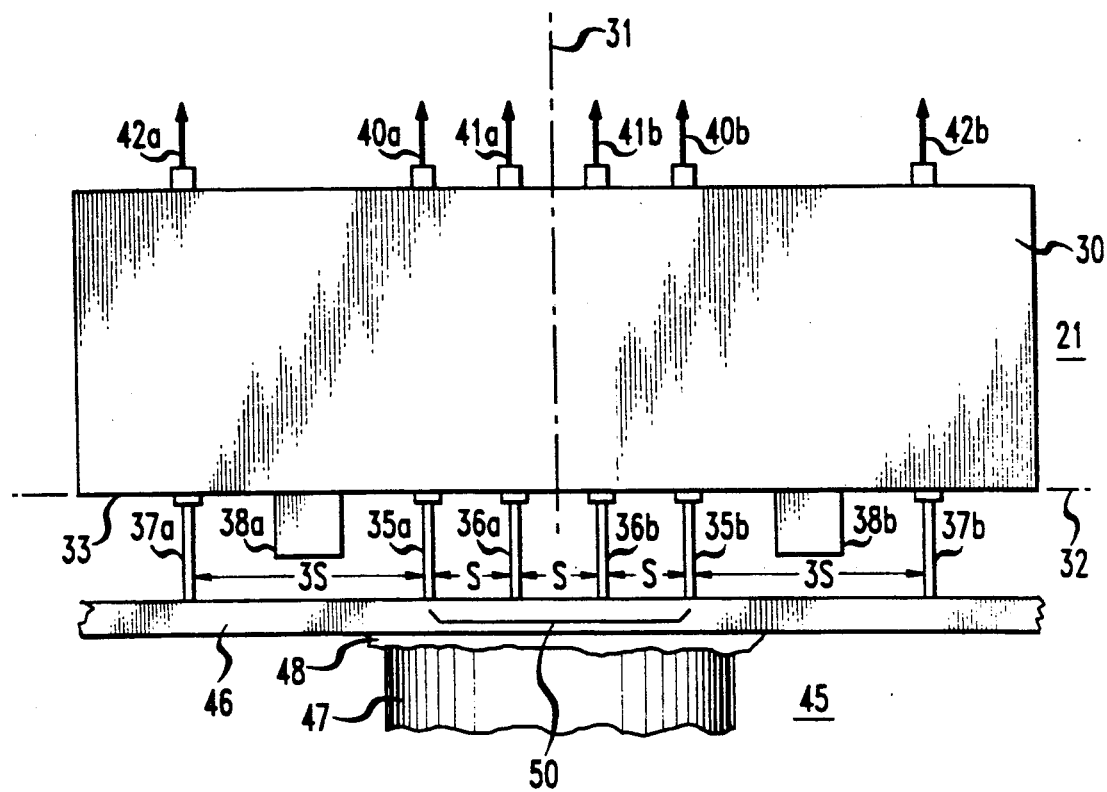
FIG. 4 is a front elevation of the FIG. 1 probe holder with the probes thereof making contact with an electroconductive body.
Figure 5:
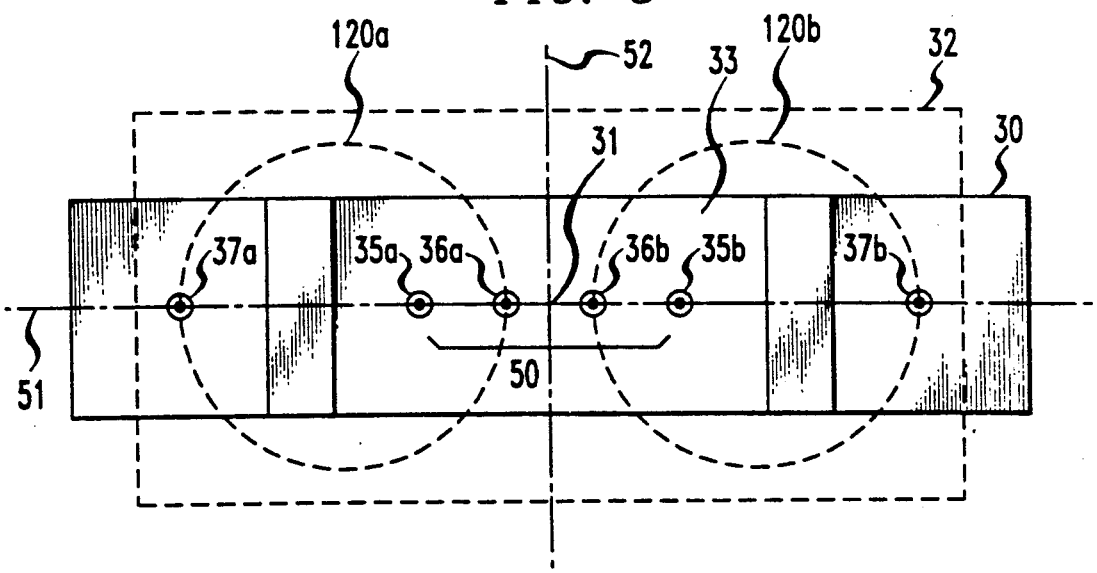
FIG. 5 is a bottom view of the FIG. 1 probe holder.

Turning now to FIGS. 4 and 5, the mounting head 21 comprises a synthetic resinous block or casing 30 having a longitudinal axis 31. Casing 30 extends in transverse and lateral dimensions in a plane 32 disposed at the front of the casing normal to axis 31. The casing has formed therein six spaced apart hole sockets (not shown) disposed transversely in line and extending from the front face 33 of the casing axially back into its interior. Those six sockets serve as receptacles for the back ends of six probes which are mounted by, and project axially forward from the front end of head 21, and which consist of a pair of current probes 35a, 35b, a pair of primary voltage probes 36a, 36b and a pair of secondary voltage probes 37a, 37b. The probes 36 and the probes 37 are called primary probes and secondary probes not for the purpose of ranking them in importance but merely for the purpose of distinguishing them in referring to them by name. All six probes at their front ends taper convergently to sharp tips to enable each of such probes to make a point contact with a surface engaged thereby. Moreover, all six probes are biased forward to fully extended limit positions by respective compression springs (not shown herein) which are contained in the sockets for such springs and which may be similar to the springs shown in the *Materials Evaluation* article as biasing forward the four probes depicted in that article. Each of the probes 35, 36, 37 is, by virtue of the action of the associated compression springs, adapted upon pressure engagement with a surface to yieldably retract into its socket under forcing from such surface and to spring back to fully extended position upon termination of such engagement. A pair of stops 38a, 38b mounted on head 30 transversely inward and outward of, respectively, probes 37 and probes 35 serve to limit the extent by which casing 30 can be advanced toward a surface engaged by the probes and, thus, the extend to which the several probes can be forced back into their sockets by such an engagement. Because the probes 35, 36, 37 are so yieldably retractable in the longitudinal or axial direction, they are adapted to make simultaneous point contacts with a surface having a non-planar configuration in that direction.

The six probes 35a, 33b, 36a, 36b, 37a, 37b are electrically connected at their back ends to six respectively corresponding leads 40a, 40b, 41a, 41b, 42a, 42b adapted to couple such probes to current means later described herein.

FIG. 4 shows the probes 35, 36, 37 as all making contact with an electroconductive body 45 for the purpose of performing an evaluation involving a resistive condition of such body. Such a body may be constituted of either the entirety of a mechanical part, structural assemblage or other discrete product to be evaluated or, alternatively, it may be constituted of only a region or portion of such part, assemblage or product. In FIG. 4, the electroconductive body 45 to be tested is depicted as consisting of a horizontal portion 46 of a metallic plate and a top portion 47 of a vertical solid metallic rod of which its portion 47 is spot welded to the bottom of plate 46 to form a weld nugget 48.

The two current probes 35 are spaced apart by a transverse gap 50, are equidistant from axis 31, and they operably form what is known as a current dipole defined by such gap and by a dipole centerline 51 passing through the axis of such current probes and the longitudinal axis 31. The gap 50 is bisected by a lateral line 52 passing through axis 31. The four voltage probes 36a, 36b, 37a, 37b are all (FIG. 5) on line 51. The primary voltage probes 36a, 36b are equidistant from axis 31 and transversely disposed between and on the inside of the current probes 35a, 35b, whereas the secondary voltage probes are transversely disposed equidistant from axis 31 on the outside of current probes 35a, 35b on the sides thereof away from gap 50. The six probes have between them the particular spacing that the inner primary voltage probes are separated from each other by the distance s, the two current probes are each separated from the nearer primary voltage probe by the distance s, and the two outer secondary voltage probes are each separated from the nearer current probe by the distance 3s. The manner in which such spacings were arrived at will be later discussed in detail.

The probes 35, 36, and 37 are, when in use, serviced by a signal processor 60 comprising (FIG. 2) a current source 61, voltage signal generating units 62a, 62b, a bias signal source 63, a computer 64, an output means 65, and a start circuit 66 for initiating performance by the processor 60 of one testing cycle of operation. Computer 64 internally provides digital integrator circuits 67a, 67b, a clock 68, a comparator circuit 70, and validity check circuits 71a, 71b.

Figure 3:
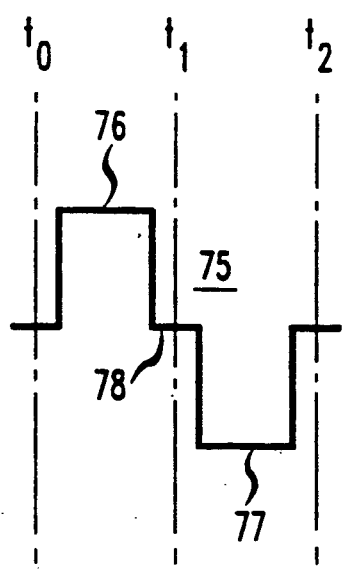
FIG. 3 is a diagram of a waveform of current produced by the FIG. 2 apparatus.

The current probes 35a, 35b are electrically connected by their leads 40a, 40b to the current source 61 which is designated herein a constant current test wave source because it is of a design to produce a flow through probes 35 of a current maintained by circuit 61 at a fixed predetermined magnitude independent of the value of the resistance presented between such probes of the path for current between them through an electroconductive body. Each test cycle is initiated in the FIG. 2 apparatus by the pressing of a button causing start circuit 66 to send a start pulse to computer 64. Prior to the initiation of such cycle, all of the probes on the head 21 are brought into contact with the body 45 then being tested (as depicted in FIG. 4). During the cycle, source 61 is triggered by clock 68 at a time $t_o$ in such cycle to generate a bipolar current pulse 75 (FIG. 3) which comprises two consecutive current square waves 76 and 77 which are of equal magnitude and duration but of opposite polarity, and which are separated by a short time interval 78.

The passage of current pulse 75 through body 45 produces at the points on its surface contacted by voltage probes 36a, 36b, 37a, 37b, a responsive set of respectively corresponding bipolar voltage pulses similar to current pulse 75 in wave shape and duration but having various magnitude values which are designated herein as $V_a$, $V_b$, $V'_a$, $V'_b$, respectively, and which are voltage values in relation to some common reference voltage such as ground. Signals of the voltages $V_a$ and $V_b$ sensed by primary voltage probes 36a, 36b are supplied via leads 41a, 41b to the inputs of an amplifier stage 80a included in unit 62a and responding to those signals to produce at its output a bipolar pulse similar in wave shape and duration to pulse 75 but representative in magnitude of the voltage $V_a - V_b = V_p$. Such pulse is sent to the A/D converter 81a included in unit 62a. Converter 81a operates under the control of clock 68 on the received $V_a - V_b$ pulse over the duration of each of its initial and final square waves (within the time intervals $t_1 - t_0$ and $t_2 - t_1$, respectively) to derive from each of such square waves a train of analog sampling pulses individually of much shorter duration than the square wave. The converter next quantizes the absolute analog value of each sampling pulse in each train into a digital binary word representation of the same value, and the converter then supplies to the digital integrator circuit 67a in computer 64 the resulting binary digital numbers representing the absolute magnitude values of all such sampling pulses. Circuit 67 mathematically integrates such numbers to feed to comparator 70 a binary digital signal of the value $V_a - V_b$.

In contrast to the amplifier 80a which is fixed as to the voltage signals it can receive at its two inputs, the amplifier 80b in unit 62b can receive at its inputs a variety of such signals. Specifically there is interposed between such inputs and the leads from the voltage probes a pair of single throw double pole switches 85, 86 respective to those two inputs. If switches 85 and 86 are thrown so that their movable contacts are as shown in FIG. 2, then amplifier 80b will receive inputs of signals $V'_a$ and $V'_b$ and produce an amplified output representing $V'_a - V'_b = V'_s$. If, however, the movable contact of switch 85 is thrown leftward from its shown position, amplifier 80b will receive inputs of signals of $V'_a$ and $V_b$ to yield an amplified output representing $V'_a - V_b$ while if, instead, switch 86 is thrown rightward from its shown position, amplifier 80b will receive inputs of signals of $V_a$ and $V'_b$ to yield an output representing $V_a - V'_b$. Otherwise amplifier 80b, A/D converter 81b, and digital intergrator 67b operate the same way as do elements 80a, 81a, and 67a as previously described. It follows that integrator 67b is adapted to supply to comparator 70 a binary digital signal which represents $V'_a - V'_b$ or $V'_a - V_b$ or $V_a - V'_b$ in dependence on how switches 85 and 86 are thrown. As will be later discussed in more detail, the voltage values $V'_a - V_b$, $V'_a - V_b$ and $V_a - V'_b$ when developed in accordance with the invention will be exact or approximate equivalents of each other.

Comparator 70 is a circuit of a kind adapted to combine the input signals thereto from integrators 67a and 67b and perform a subtraction operation with respect to the values of such two signals so as to obtain a resultant signal which a function of the difference between such values. Hence, assuming that the binary signal supplied from integrator 67b to comparator 70 is representative of the value $V'_a - V'_b = V_s$, comparator 70 will provide to output 65 a resultant signal as a function of the quantity $V_s - V_p$. Comparator also, however, receives from bias signal source 63 a binary bias signal representative of a voltage $V_k$ of a value which can be selectively set by manual adjustment of a control for source 63, but which will then remain constant at that selected value. Hence, the mentioned resultant signal is, more specifically, representative of the quantity $V_k + (V_s - V_p)$.

The output 65 which receives such resultant signal produces an output comprising information about the electroconductive body being evaluated. Output 65 can take a variety of forms. For example without restriction, it may be a meter adapted to provide an output in the form of a visual indication of the value of the quantity $V_k + (V_s - V_p)$. As a further example without restriction, output 65 may be a signal transfer means adapted to transmit a signal which, say, is utilized further on to produce automatic rejection of the item comprising the tested electroconductive body 45 if the quantity $V_k + (V_s - V_p)$ does not meet one or more numerical criteria pre-established therefor.

The output unit 65 is coupled to the two validity check circuits 71a, 71b which are respectively associated with the digital integrators 67a and 67b. Validity check circuit 71a operates to compare the signal $V_a - V_b$ yielded by integrator 67a to lower and upper limit thresholds for such signal. If such signal is affected by a spurious factor (or factors) so as to not fall in the range between such thresholds, circuit 71a controls output unit 65 to override and suppress the output which would normally be provided thereby, and to cause that unit to instead indicate that the test being conducted in that particular test cycle is a failure in the sense that the output which would be derived from the test would be invalid. An example without restriction of a case in which such a spurious factor would be present is the instance where one of the voltage probes from which the voltage signals are derived does not make proper contact with the electroconductive body 45. Validity check circuit 71b operates, in a similar way to that just described for circuit 71a, to control the output from unit 65 in the case where the voltage differential signal yielded by integrator 67 does not fall in the range between lower and upper thresholds set for that signal. The presence in the FIG. 2 system of the validity check circuits is desirable because of various testing applications of that system in which (as will later herein become more apparent) the resultant signal produced by comparator unit 70 will tend to suppress the effects on the value of that signal of a spurious factor or factors such that the presence thereof is concealed and will not be recognized. In contrast, in the four-part probe technique described in the *Materials Evaluation* article, a spurious factor operating on the signal derived from the two voltage probes during a test cycle will likely produce an abnormally great departure in the value of such signal from normal so that the presence of a spurious factor affecting the signal value can readily be recognized.

We come now to the matters of the selection of the appropriate spacings between the various probes mounted by holder 20 and the effects of such spacings on the voltages sensed by the voltage probes. Such selection is accomplished by the technique of providing an actual or deemed application of current probes 35 to a surface of a template element in an operating cycle of the FIG. 2 system, determining the geometry of equipotential contours produced on such surface from the flow or deemed flow of current through such element between such probes, and locating as a function of such geometry the secondary voltage probes relative to each other and to the primary voltage probes and current probes. While such technique can be carried out experimentally, it is easier (and fully adequate in many applications) to do it mathematically as follows.

Figure 6:
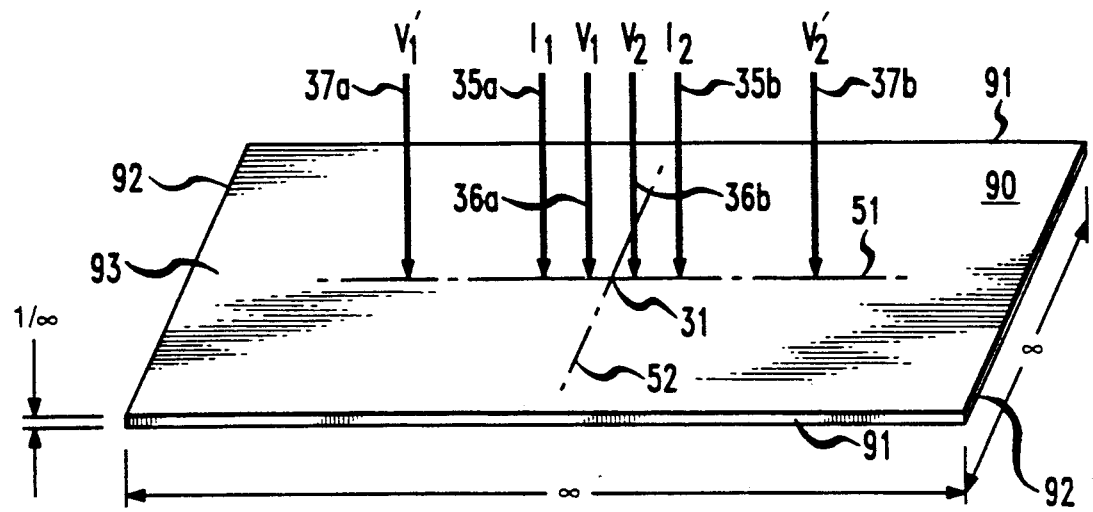
FIG. 6 is a schematic isometric view of a representation of a deemed contact of the probes of the FIG. 1 probe holder with a mathematically postulated template sheet.

Referring to FIG. 6, what is shown thereby is a mathematical representation of the probes 35, 36, 37 of the FIG. 2 apparatus making contact with a template element consisting of a planar resistive sheet 90 which is homogeneous in resistivity throughout, and which is idealized in that its transverse and lateral boundary edges 91 and 92 are infinite in length, and the sheet is of infinitesimal thickness w beneath its upper surface 93. Sheet 90 is, of course, a mathematically conceived template sheet.

An article by F. M. Smits entitled "Measurement of Sheet Resistivities with the Four-Point Probe" and published in May 1958 on pages 711-719 of the Vol. 37, No. 3 issue of the *Bell System Technical Journal* discloses an arrangement similar to that represented in FIG. 6 except that there are only two voltage probes (corresponding to the primary voltage probes 36 hereof). Such article sets out that, where current is passed through an infinite resistive sheet between probes providing a current dipole for the sheet, the voltage produced by such current flow is given by the expression $$I(\rho_s/2\pi) \cdot \log(r_1/r_2) \qquad (1)$$

where I is the current, $\rho_s$ is the sheet resistivity, and $r_1$ and $r_2$ are the distances from the +current source and the −current source. I have discovered that such expression can be given a geometric significance in two dimensions and can be used as a mathematical underpinning for a technique I have developed to compute and plot equipotential contours on the sheet's surface contacted by the probes. The manner of so doing is shown in FIG. 7 which is another depiction of the FIG. 6 arrangement of the probes 35, 36, 37 and the infinite resistive sheet 90.

The computation is started by picking in FIG. 7 a point on sheet 90 which is preferably (but not necessarily) transversely between the current probes 35 and is on the dipole center line 51. One such point which will be used as an example herein is the point of contact with sheet 90 of the primary voltage probe 36a. Having chosen that point, its respective distances $r_1$ and $r_2$ from the ones of current probes 35a and 35b which are nearer to and farther from that point, respectively, are determined and, in the case of point 36a, such distances are equal to, respectively, s and 2s.

As the next step, there is drawn from current probe part 35a a first sequence of circular arcs 94a each having a radius 95a of $y(r_1)$ where y is a variable having a different assigned value for each of such arcs. There is then drawn from current probe part 35b a second sequence of circular arcs 94b each having a radius 95b of $y(r_2)$ for such different assigned values for y. Such arcs of such second sequence respectively correspond to those of such first sequence to result in a sequence of pairs of arcs with the pairs of arcs in such sequence being respectively associated with different assigned values for y. Each such pair of arcs consists of those arcs from the first and second sequences for which y has the assigned value, specifically associated with that pair and used to determine the sizes of the respective radii for such two arcs.

The two arcs in each such pair of arcs are adapted to intersect each other and are drawn to so intersect to produce on sheet 90 a particular intercept point 96 for that one pair. There is thus produced on sheet 90 a plurality of such intercept points 96 corresponding to the mentioned sequence (or plurality) of pairs of arcs obtained.

The final step is to fit a curving line to pass through all of such intercept points 95. The result will be a closed curve 101a (FIG. 8) which (a) is defined on the surface 93 of template sheet 90, (b) surrounds the current probe 35a, and (c) is an equipotential contour in the sense that all points on such contour will manifest the same sensed voltage produced by the action of the current dipole. To put it another way, such contour is the locus of all points on surface 93 having the same voltage on account of the action of such dipole. One such point on such contour is, of course, the point of contact of primary voltage probe 36a with surface 93 which is used as the starting point for computing and plotting that contour.

FIG. 7 also shows, as another example, the steps involved in computing and plotting the equipotential contour 101b (FIG. 8) on template surface 93 on which contour is located the point of contact of primary voltage probe 36b with that surface. For the purpose of defining that contour, contact point 36b has distances of $r_1 = s$ and $r_2 = 2s$ from respectively the current probe contact points 35b and 35a, respectively. Sequences of arcs 97b, 97a having radii 98b, 98a of sizes $y(r_1)$ and $y(r_2)$ are drawn from, respectively, the points 35b and 35a as centers for such arcs to produce in a manner analogous to that described above a set of intercept points 99 which define such contour 101b. The technique described above for computing and plotting equipotential contours does not require that the point used as the starting point for developing the contour be in the gap 50 between center probe points 35a, 35b on the dipole center line 51. It is, though, convenient that the starting point be in that segment of line 51. Contours, however, can be plotted for any number of starting points in that line segment. Thus, there can be defined on the surface 93 a whole pattern or map of equipotential contours calculated as produced by the flow of current through template 90 between the current contact points 35a, 35b.

Figure 8:
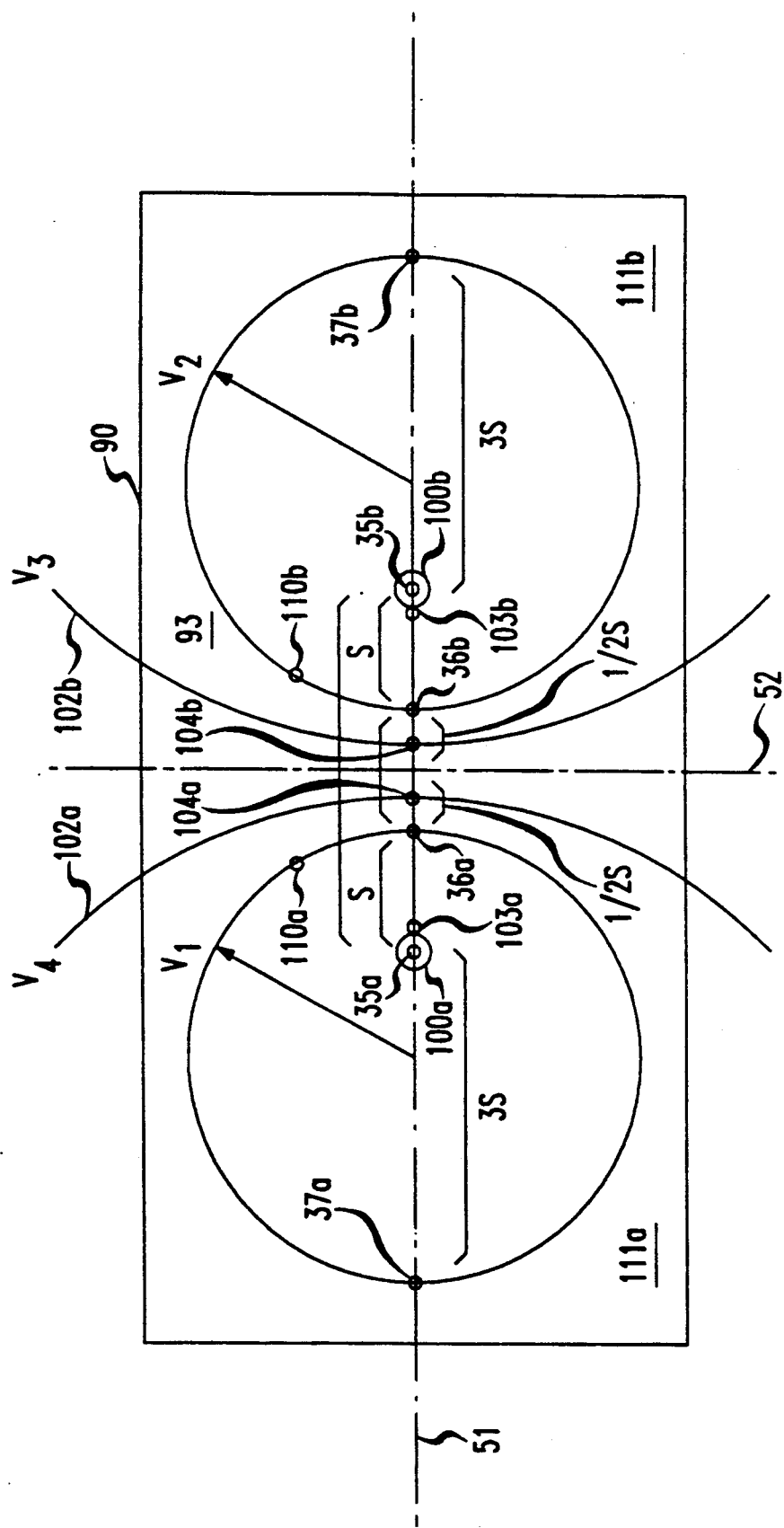
FIG. 8 is a diagram of sets of equipotential contours resulting from application of the FIG. 7 method.

FIG. 8 shows such a map of contours divided into two sets of which the set of contours 100a–102a surrounds current probe point 35a, and the set of contours 100b–102b surrounds the current probe point 35b. Contours 101a and 101b have thereon the primary probe voltage points 36a and 36b. The smallest contours 100a, 100b intersect dipole center line at points 103a, 103b thereon which can be used as starting points for computing such contours, and which points are closer to the nearest current probe points thereto (i.e., points 35a, 35b) than are the primary probe points 36a, 36b. The largest curved contours 102a, 102b intersect line 51 at points 104a, 104b which are farther from the current probe points respectively nearest thereto than are the primary voltage probe points.

The various contours shown in FIG. 8 may have different voltage values assigned thereto because of differences in the value of the current postulated as flowing through that sheet between the current probes (and/or the value of the resistivity postulated for sheet 90). However, the geometry of the individual contours and the pattern of the contours will remain the same despite such differences in electrical parameters. Maps of contours defined on the same infinite sheet by pairs of current probes having different spacings between them (i.e., different dipole lengths) will be similar but not congruent. Such maps can, nonetheless, be normalized and made congruent by dividing the distances on each map by the size used for that map of the gap between the current probes. The map of equipotential contours shown by FIG. 8 thus has a universal quality.

The closed-curve equipotential contours described above are circles of which the radius of each is set out by the expression $$R = \frac{r_2 r_1}{r_2 - r_1} \quad (2)$$

under the conditions that $$r_1 + r_2 = G \quad (3)$$

and $$0 < r_1 < r_2 \quad (4)$$

where G is the size of the gap 50, and where $r_1$ and $r_2$ are the displacements of the intersection of the contour with line 51 from the ones of current points 35a, 35b which are, respectively, nearest to and farthest from that point of intersection. If in (1), $r_1 = r_2$, then R becomes infinite. It follows that in FIG. 8 the dipole bisecting line 52 (which is the locus of all points on surface 93 for which $r_1 = r_2$) is also representative of the arcs of each of two circular contours of infinite radius and of which one and the other encircle, respectively, the current probe point 35a and the current probe point 35b.

With the radius of the contour circle being given by (1) and it being evident from that, except in the limiting case where $r_2 = r_1$, the radius R must be greater than $r_1$, the expression follows that:

$$c = R_1 - r_1 \quad (4)$$

where c is the distance along line 51 in the direction away from gap 50 of the center of such circle from such current probe point. Expressions (1) and (2), however, fully define the radial size and center position of every circular equipotential contour which can be defined on template surface 93.

Applying expressions (1) and (2) to the circular contours 101a, 101b on which are the primary voltage probe points 36a, 36b, it is shown in FIG. 8 that both contours have a radius of $R = 2s$ and that the centers of both contours are displaced outward of the corresponding current probe points 35a, 35b by the distance $c = s$.

Another important feature shown by FIG. 8 is that, because the secondary voltage probe points 37a, 37b are spaced by 3s outward of the current points 35a, 35b and are hence 2s outward of the centers of contours 101a, 101b which have radii of 2s, those secondary voltage points are located on those equipotential contours on which are also the primary voltage points 36a, 36b. Consequences of this are that (a) upon deemed application of the current probes 35a, 35b to template 90 to produce current flow through it and resulting voltages manifested in the template surface 93, the voltages $V'_a$ and $V'_b$ sensed at points 37a, 37b will be the same, respectively, as those sensed at points 36a, 36b, (b) whence, assuming that, in the FIG. 2 system, switches 85 and 86 are thrown to connect amplifier 80b to receive inputs of $V'_a$ and $V_b$, the voltage differential signals of $V'_a - V'_b$ and $V_a - V_b$ from amplifiers 80b and 80a will be the same in value, whence (c), the resultant signal of $(V'_a - V'_b) - (V_a - V_b)$ from comparator 70 will have a value of zero.

A significant conceptual point here is that, although the resistivity of template 90 may be postulated to have widely different values, and although such widely different resistivity values would be reflected in corresponding widely different values at such different times for the individual voltages $V_a$, $V_b$, $V'_a$, $V'_b$, and the differential voltages $V_a - V_b$ and $V'_a - V'_b$, nonetheless, because in the output from comparator 70 the voltage value $V_a - V_b$ is offset by $V'_a - V'_b$ the effects of such resistivity changes on the value of the resultant signal are (ignoring any effect from the correcting signal $V_k$) cancelled out either largely or entirely. Complete cancellation occurs when the points 37a, 37b which yield the voltages $V'_a$ and $V'_b$ are on the same equipotential contours as respectively the points 36a, 36b which yield the voltages $V_a$ and $V_b$ so that $V'_a$ is necessarily the same as $V_a$ and $V'_b$ necessarily the same as $V_b$, and the voltages $V'_a - V'_b$ and $V_a - V_b$ are then necessarily equal to each other.

As to how the voltages $V'_a - V'_b$ and $V_a - V_b$ can be equal to each other despite the much greater spacing between points 37 than between points 36, a better understanding of that matter may be gained by regarding what happens to be the following. As current passes between the current probes through non-anomalous template 90, portions of such current will flow through all points of the template to and/or from each current probe in all radial directions emanating from that probe. The voltage $V_a - V_b$ can be deemed to be produced by current flowing between points 36a, 36b through template 90 in a first distributed current path which is relatively short in effective length and effective cross-section. The voltage $V'_a - V'_b$ can be deemed to be produced by current flowing between points 37a, 37b in a second distributed current path which is much longer in effective length than the first, but which compensates for that greater length by having a much greater effective cross-section than the first path. The result is that both paths offer the same apparent resistivity to current flow between the voltage sensing points between which such two paths resectively extend.

There has so far been considered the balancing of the voltage $V_a - V_b$ generated between points 36a, 36b by the voltage $V'_a - V'_b$ only when such latter voltage is generated between the points 37a, 37b which, like the points 36a, 36b, are on the dipole center line 51 and, further, are displaced as far away as possible from points 36a, 36b around the equipotential contours 100a, 100b. In point of fact, however, the successful working of such balancing (to produce full or partial cancellation of voltage values) does not require that either the primary voltage points or the secondary voltage points be on dipole line 51, or that the intercepts with such line of the equipotential contours on which such points are located have any special positions in gap 50 relative to the current probes. Instead, such voltage points can be disposed at discretion laterally off that line and transversely away from the shown locations of points 36 and 37. All that is required is that each secondary voltage point is substantially on the same equipotential contour as that on which the corresponding primary voltage point is positioned. Thus, for example, the primary voltage probes could be located at the points 110a, 110b (FIG. 8) and/or the secondary voltage probes could be located at the points 111a, 111b. In order, however, for the distributed current path between the secondary points to be substantially different from the distributed current paths between the primary points, it is preferred that each secondary point be substantially displaced from the corresponding primary point around the equipotential contour common to both points. In FIG. 8, the primary and secondary points 36 and 37 are optimally located to make the primary and secondary distributed current paths as different as possible from each other.

As another matter, the benefits of the invention can be realized by the use of only three voltage probes instead of four. To wit, inasmuch as the primary point 36b is on the same equipotential contour as is the secondary point 37b, the differential voltage $V'_a - V_b$ between points 37a and 36b will be the same as the differential voltage $V'_a - V'_b$ between points 37a and 37b so that, as already described in the FIG. 2 system, the former voltage differential can, by manipulation of switch 85, be validly substituted in the system for the latter differential to thus permit the elimination altogether of voltage probe 37b. For the same reason, if it is desired to instead eliminate probe 37a instead of the probe 37b, the voltage differential $V_a - V'_b$ can, by manipulation of switch 86, replace the voltage differential $V'_a - V'_b$ so that probe 37a is not needed to produce a differential voltage suitable for combining in comparator 70 with the voltage differential $V_a - V_b$. In general, in order to provide in the resultant signal from unit 70 the full or partial cancellation discussed, only three voltage probes are needed to provide to that unit input signals of two voltage differentials suitable to realize such cancellations by the combining of such signals. Such two suitable voltage differentials will be produced among such three probes when they are relatively positioned so that a first and a second of them are substantially on the same equipotential contour in substantially displaced relation from each other around that contour, and so that the third of such probes is substantially displaced away from such contour, and when, further such two voltage differentials are those existing between, on the one hand, such first and third probes and, on the other hand, such second and third probes. Again, however, it is preferred to obtain the two voltage differential for which input signals are supplied to comparator unit 70 from, on the one hand, two primary voltage probes and, on the other hand, two secondary voltage probes in order to better assure that the distributed current paths between the two points yielding one and the other of such two voltage differentials will be paths through template 90 which are substantially different from each other.

Figure 9:
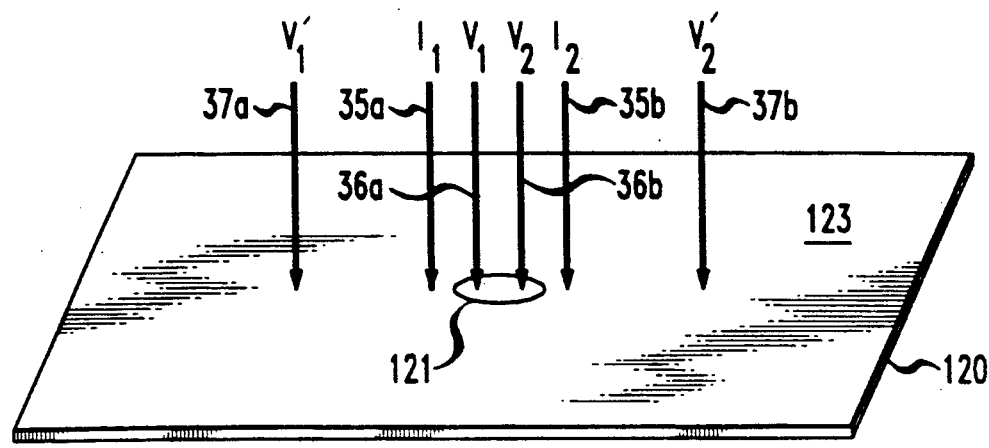
FIG. 9 is a schematic isometric view of a deemed contact of the probes of the FIG. 1 holder with the mathematically postulated FIG. 6 sheet when such sheet contains a resistive anomaly.

As so far described, the information which would be yielded by the deemed application of the FIG. 2 system to template 90 would be of no value since such template is presupposed to be a homogeneous non-anomalous resistivity medium, and the balancing in comparator unit 70 of the two voltage differential input signals against each other to yield a zero value output would merely confirm such presupposition. FIG. 9 depicts, however, a different situation in which the wholly non-anomalous template 90 has been replaced by another mathematical template sheet 120 in which, as before, the sheet is planar and has transverse and lateral boundaries of infinite length and is of infinitesimal thickness, but which template 120 includes an area 121 of anomalous resistivity and containing within its perimeter both of the points of contact with the surface 123 of such template of the primary voltage probes 36a, 36b. The area 121 may be representative, for example, of a spot weld. The effect of the presence in template 120 of area 121 is to distort the pattern of equipotential contours defined on the template surface 123 relative to the analogous pattern of equipotential contours defined on the surface 93 of the template sheet 90 shown in FIG. 6, and of which a representation of such pattern is given by FIG. 8. The greatest such distortion will appear within area 121 within which the primary probes 36 are located, but there will even be some such distortion much further out where the secondary voltage probes are located. As a result of such distortion, such secondary probes 37a, 37b will no longer be substantially on the same equipotential contours as their respectively corresponding primary probes 36a and 36b. Accordingly, in the output signal of the comparator unit 70, the quantity represented by that signal of $(V'_a-V'_b)-(V_a-V_b)$ will depart significantly in value from zero, and that departure will constitute an indication of the presence of the anomalous resistivity area 121. The voltage differential $V_a-V_b$ in that quantity will have a value in the FIG. 9 case which is changed substantially from its value in the FIG. 6 case because area 121 constitutes a major part of the distributed current path between primary voltage probes 36. The voltage differential $V'_a-V'_b$ will also undergo a change in value in going from the FIG. 6 case to the FIG. 9 case, but such latter change will be slight inasmuch as the area 121 occupies in the FIG. 9 case only a minor part of the distributed current path between secondary voltage probes 37. More important to note is that in FIG. 9 the non-zero value obtained for the quantity $(V'_a-V'_b)-(V_a-V_b)$ is determined almost entirely by the effect on the current flow through the template of the presence of area 121 and only to an insignificant extent as the effect of the background anomalies which might be present such as, for example, a background change in the resistivity of the template sheet material throughout the entire template. That is so because, as earlier described, the effects of such background anomalies on such quantity value are largely or wholly cancelled out. The value derived by the FIG. 2 system for the quantity $(V'_a-V'_b)-(V_a-V_b)$ is thus adapted to provide a highly sensitive indication of the presence (or degree of presence) of a particular localized anomaly in an electroconductive body being tested.

The foregoing analysis involving FIGS. 6-9 is used to determine advantageous positioning of the probes carried by the described probe holder 20 in a manner as follows. Referring to such holder as shown by FIGS. 4 and 5, and starting with the current probes 35a and 35b which have the same mutual spacing as do the current probe contact points 35a, 35b shown in FIG. 8, it is assumed that (a) each of such current probes is encircled by a set of closed loops each defined by a curved line extending transversely and laterally in space to close upon itself and surround that current probe, and (b) each such closed loop coincides one-for-one in size and shape with one of the equipotential contours which surrounds the contact point of that current probe when deemed to contact a template element as described, and (c) such contour is on the contacted surface of that template element. FIG. 5 shows two such closed loops 120a, 120b which both extend laterally and transversely in plane 32 to surround the current probes 35a and 35b, respectively, and which loops 120a, 120b coincide one-for-one in size and shape with, respectively, the equipotential contours 101a and 101b depicted by FIG. 8 as defined on the surface 93 of the postulated template sheet 90. The sets of closed loops thus postulated as respectively surrounding the two current probes on probe mounting head 30 are then utilized to position the voltage probes on head 30 relative to each other and to the current probes. Specifically, such voltage probes are positioned transversely and laterally relative to such closed loops in the same way as the voltage contact points shown in FIG. 8 are positioned relative to the equipotential contours shown therein in order (as discussed above) to reduce towards zero or to zero the value of the quantity $(V'_a-V'_b)-(V_a-V_b)$ or the value of the equivalent quantity obtained when only three voltage probes are used. A consequence of this approach is that, in the embodiment disclosed herein, all of the voltage probes 36a, 36b, 37a, 37b are located on the dipole centerline 51, the secondary probes 37a, 37b are at positions on or substantially on the closed loops 120a, 120b on which are located the primary probes 36a, 36b respectively corresponding to those secondary probes, the primary voltage probes have the same spacing s from each other as they do from the current probes, and four instead of three voltage probes are used, all because such a positioning configuration for the voltage probes is an optimum one for reducing towards or to zero the value of the mentioned quantity when the template 90 is used as a mathematical representation of an actual electroconductive body being tested. As pointed out in connection with FIG. 8, however, there are numerous alternative voltage probe positioning configurations which can be used to further the objective of reducing the value of that quantity. Also, such objective can be furthered by the use of only three voltage probes. To put it another way, the discussion regarding appropriate positioning in FIG. 8 of voltage points in order to reduce the value of the mentioned quantity is to be taken as applying to the lateral and transverse positioning on head 30 shown in FIG. 5 of the four voltage probes 36a, 36b, 37a, 37b, or at least three of them.

As stated, such voltage probes when positioned as shown in FIG. 5 have an optimal positioning, relative to each other and the current probes for testing electroconductive bodies when the template 90 is an acceptable mathematical representation of the body 45 being tested. It has been found that such template is an acceptable such representation when such body is primarily a planar sheet which is substantially homogeneous in resistivity except possibly at the location where the existence of an anomaly is being tested for, and which has transverse and lateral dimensions greater than 10s and a thickness less than 0.5s where s is the spacing between primary voltage probes in the probe configurations shown in FIGS. 5 and 8. Even, however, where the tested body 45 meets these criteria, that body has finite boundaries and a finite thickness which both constitute factors which may well affect to different extents the apparent resistivities of the distributed current paths through the body between respectively the voltage probes 36 and the voltage probes 37. If, however, such apparent path resistivities are so affected differently, then the value of the quantity $(V'_a-V'_b)-(V_a-V_b)$ will no longer be zero even if there is no localized anomaly present in the test body. That is, such factors (with or without accompanying lack of configurational compliance of the body with planar template 90 or of homogeneity of the body outside of the tested area) can be considered in that case to introduce into the voltage value represented by that quantity an error voltage component along with the "authentic" voltage component indicating the extent or presence of the localized anomaly (e.g., a defective spot weld) being tested for.

One way of dealing with the possible creation of such an error is to utilize in FIG. 8 a mathematical template element better conforming to the body 45 than does planar template 90 in respect of configuration, homogeneity and/or finite geometric boundaries, to mathematically calculate the relevant equipotential contours on such replacing template element, and to otherwise proceed as described above to determine the spacing of the voltage probes relative to each other and the current probes. For example, if a set of electroconductive bodies to be tested for structural defects are in the form of segments of thin spherical shells, the mathematical template element used in the above-described FIG. 8 procedure may be one which is in the form of a spherical shell segment similar in size and shape to such bodies. While utilizing mathematical templates other in form than sheet 90 as representations of bodies to be tested to the end of reducing the mentioned error is an approach included within the invention hereof, it has the difficulty that the mathematics needed to compute the relevant equipotential contours becomes quite complicated.

An alternative approach directed to the end of reducing such error is to substitute in FIG. 8 for the mathematical template 90 a physical template element and to establish experimentally the geometry of the equipotential contours defined on the contacted surface of such physical template when current is passed through the template between the current probes 35. Such as physical template need not be planar, would have finite dimensions and can have any appropriate size and shape. It could be, for example, a non-defective sample of the set of electroconductive bodies to be tested. While such alternative approach is included in the invention hereof, the drawback in such approach is that to plot such contours experimentally on a physical template is very laborious.

Accordingly, it is preferred that the problem of dealing with the error voltage component possibly included in the total voltage value of the quantity $(V'_a - V'_b) - (V_a - V_b)$, or equivalent quantity, be dealt with electrically. Specifically, rather than using either of such just described two approaches which would both end up with adjusting the voltage probe spacings for the particular case (or from case-to-case) to the end of eliminating such error component, I prefer to base such spacings on the use of the template 90, to use such spacings for all testings by the FIG. 2 system and to compensate for any such error component in the quantity $(V'_a - V'_b) - (V_a - V_b)$ by combining in comparator unit 70 the signal representing that quantity with a bias signal from source 63 representing a value equal and opposite to such error component. The result of such combining will then be that the effect of the error on the resultant signal from unit 70 will be fully cancelled by the effect on such signal of the bias signal to thereby cause that resultant signal to compensate fully for any error generated in the mentioned quantity because of departures of characteristics of individual bodies 45 in a set thereof being tested from the characteristics of the non-anomalous template 90. The proper value for the bias signal may be determined by trail and error as, say, by conducting a calibration test on a known non-defective sample of a set of bodies 45 to be tested, and by then adjusting source 63 to change its bias signal to unit 70 until the output unit 65 provides an indication (or other output), of the quantitative value selected to represent that the inspected body has, say, no defect or has such other feature as is being examined for. Note that such selected value may be zero and that the value of the output of unit 65 may vary positively or negatively from zero.

As earlier stated, the equipotential contours developed in the template sheet 90 are circles with a radius of $(r_2 r_1)/(r_2 - r_1)$ as set out by equation (2). That such is so may be proved as follows.

Figure 10:
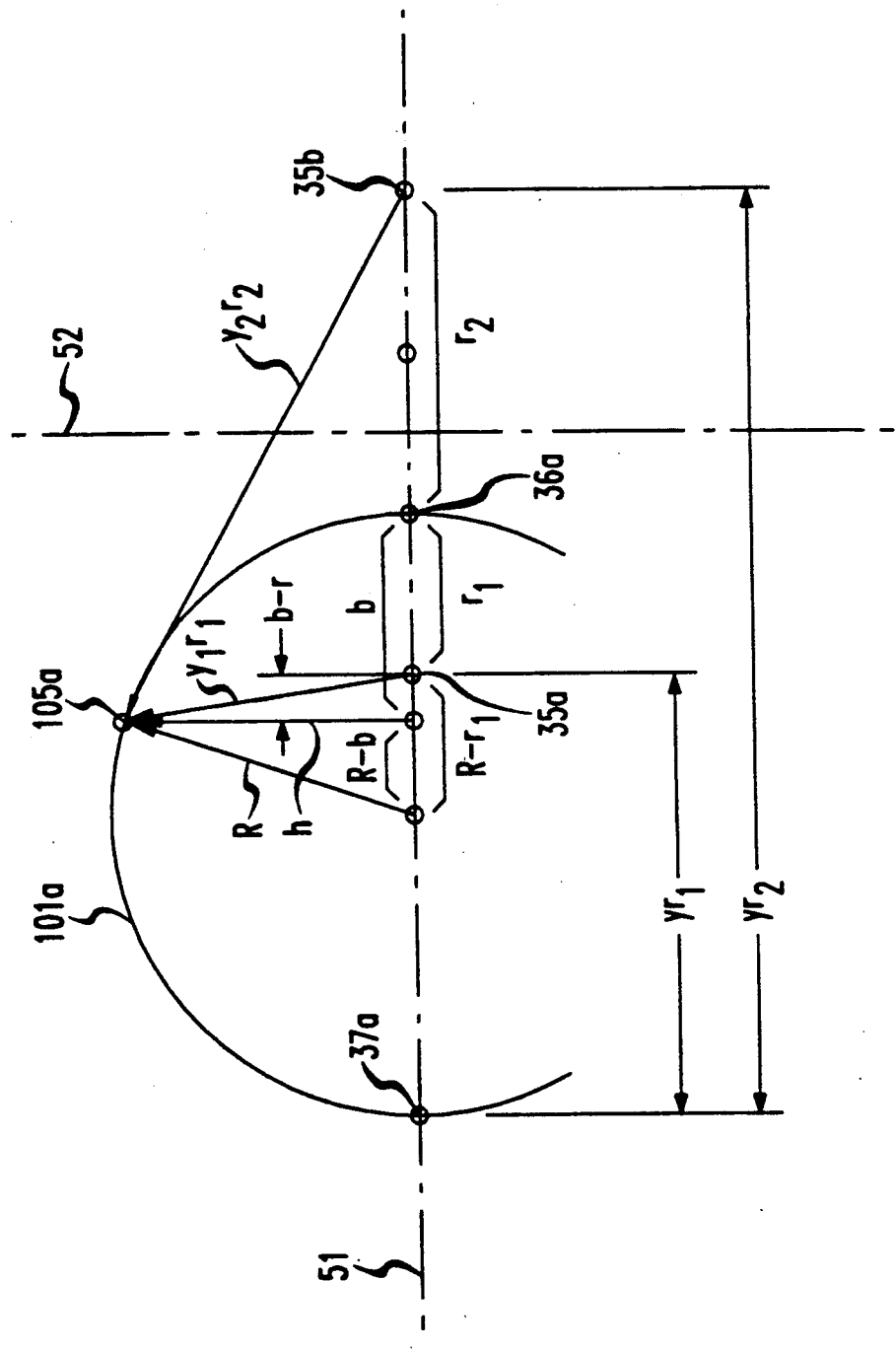
FIG. 10 is a mathematical diagram related to FIG. 8.

Referring to FIG. 10 the secondary voltage probe 37a (which is on the same equipotential contour 101a as primary voltage probe 36a, is spaced from the current probes 35a and 35b by the respective distances $yr_1$ and $yr_2$. Hence, for the point on that contour at which is located probe 37a, it is clear from FIG. 10 that:

$$yr_2 = yr_1 + r_2 + r_1 \qquad (5)$$

$$y(r_2 - r_1) = r_2 + r_1 \qquad (6)$$

$$y = \frac{r_2 + r_1}{r_2 - r_1} \qquad (7)$$

Assuming to begin with that contour 101 is a circle having a radius R, it is evident from FIG. 10 that:

$$2R = yr_1 + r_1 \qquad (8)$$

$$= \left(\frac{r_2 + r_1}{r_2 - r_1}\right) + r_1 \qquad (9)$$

$$= r_1 \left(\frac{r_2 + r_1}{r_2 - r_1} + 1\right) \qquad (10)$$

$$= r_1 \left(\frac{2r_2}{r_2 - r_1}\right) \qquad (11)$$

whence $$R = \frac{r_2 r_1}{r_2 - r_1} \qquad (2)$$

Having found the radius for an equipotential contour assuming that it is a circle, it is now necessary to prove that such assumption is correct. This is done as follows:

Draw the contour 101a as a circle so that it has a radius of R and a diameter of 2R on the dipole centerline 51 with the voltage probe contact points 37a and 36a being on such circle at opposite ends of such diameter (FIG. 10). Now take any other point 105a on such circle and construct a perpendicular h from line 51 to that point, the foot of such perpendicular being spaced from point 36a and the center of the presumed circle by the distances of b and R−b respectively. By the application of the Pythagorean theorem:

$$R^2 - (R-b)^2 = h^2 = (y_1 r_1)^2 - (b - r_1)^2 \qquad (12)$$

where $y_1$ is an unknown quantity. From (12), $$y_1^2 r_1^2 = 2Rb - 2r_1 b + r_1^2 \qquad (13)$$

$$y_1^2 r_1^2 = 2b \left(\frac{r_1 r_2}{r_2 - r_1}\right) - 2r_1 b + r_1^2 \qquad (14)$$

letting $b = k r_1$ $$y_1^2 r_1^2 = \frac{2k r_1^2 r_2}{r_2 - r_1} - 2k r_1^2 + r_1^2 \qquad (14)$$

$$y_1^2 = \frac{2k r_2}{r_2 - r_1} - 2k + 1 \qquad (15)$$

$$y_1^2 = \frac{2k r_1 + r_2 - r_1}{r_1 - r_1} \qquad (16)$$

Now, if it is the fact that the equipotential contour 101a is a circle as shown in FIG. 10, then for any point on that circle as exemplified by point 105a it must be that quantities $y_1$ and $y_2$ must be equal to each other because, as discussed in connection with FIG. 6, that equality of $y_1$ and $y_2$ was one of the criteria for calculating and plotting an equipotential contour. Conversely, a showing in FIG. 10 that $y_1=y_2$ is proof that contour 101a is indeed a circle of radius R. To make such showing, we use again the Pythagorean theoem to derive that:

$$R_2^2 - (R - b)^2 = h^2 = (y_2 r_2)^2 - (r_2 + b)^2 \quad (17)$$

$$y_2^2 r_2^2 = 2Rb + r_2^2 + 2r_2 b \quad (18)$$

$$y_2^2 r_2^2 = 2b \left( \frac{r_1 r_2}{r_2 - r_1} \right) + r_2^2 + 2r_2 b \quad (19)$$

Now letting $b = mr_2$, $$y_2^2 r_2^2 = \frac{2mr_1 r_2^2}{r_2 - r_1} + r_2^2 + 2mr_2^2 \quad (20)$$

$$y_2^2 = \frac{2mr_1}{r_2 - r_1} + 2m + 1 \quad (21)$$

$$y_2^2 = \frac{2mr_2 + r_2 - r_1}{r_2 - r_1} \quad (22)$$

$$y^2 = \frac{2mr_2 + r_2 - r_1}{r_2 - r_1} \quad (23)$$

But we know that $mr_2 = b = kr_1$. Hence, making the proper substitutions in (23) to eliminate m, we get $$y_2^2 = \frac{2kr_1 + r_2 - r_2}{r_2 - r_1} \quad (24)$$

The right hand side of expression (24) is, however, identical with the right hand side of the expression (16). Hence $y_2$ necessarily equals $y_1$, but the fact that such equality exists proves that contour 101a is a circle with radius R.

The above described embodiments being exemplary only, it is to be understood that additions thereto, omissions therefrom and modifications thereof may be made without departing from the spirit of the invention. For example, instead of comparator unit 70 being a subtractor means for combining the inputs thereto to yield a resultant signal as a function of the difference of those inputs, that unit may be a divisor means for combining those inputs to derive therefrom a resultant signal as a function of a quotient of the values of such inputs. That is, unit 70 may produce a signal as a function either of the quotient quantity $V'_a - V'_b)/(V_a - V_b)$ or an equivalent quotient quantity when only three voltage probes are used. As another example, one or both of the validity check circuits 71a, 71b may operate to suppress the output from unit 65 directly in response to one or ones of the voltages $V_a, V_b, V'_a, V_b$ (as distinct from differentials between such voltages) individually exceeding a limit or limits preestablished therefor.

Accordingly, the invention is not to be considered as limited save as is consonant with the recitals of the following claims.

I claim:

1. Apparatus for performing evaluations of electroconductive bodies comprising:
a probe holder having a longitudinal axis and a front end extending in orthogonal transverse and lateral dimensions normal to said axis, first and second current probes mounted by, and axially projecting forward from said end of, said holder and separated from each other by a transverse gap in a lateral-transverse plane, said probes being operable for the purpose of performing such an evaluation to each contact such an electroconductive body and, upon said contact, to form a current dipole defined by said gap and a dipole centerline passing through said probes, and probes being further operable for such purpose to preliminarily contact a physical sheet approximating a planar homogeneously resistive ideal template element with infinite boundaries and infinitesimal thickness and, upon passage of current through said sheet between said probe, to produce on said sheet a set of equipotential contours surrounding the point of contact of each such probe with such sheet, first and second primary voltage probes mounted by, and projecting axially forward from said end of, said holder and operable for such purpose to both contact said body concurrently with said current probes, said first and second voltage probes corresponding to, respectively, said first and second current probes and being disposed in said plane in spaced relation from each other so that each will be nearer to its corresponding current probe than to the other thereof, and each of said first and second voltage probes being at locations on, respectively, first and second closed loops respectively surrounding in space said first and second current probes, the pattern of such first and second loops being approximately the same in size and shape and location as the pattern of first and second of said contours which respectively surround the points of contact of said first and second current probes with said sheet, and at least a first secondary voltage probe mounted by, and projecting axially forward from said end of, such holder and adapted to contact said body concurrently with such current and primary voltage probes, said first secondary voltage probe corresponding to said first current probe and being disposed substantially on said first closed loop at a position thereon displaced substantially around such loop from the location of said first primary voltage probe on such loop.

2. Apparatus according to claim 1 in which said first primary voltage probe is transversely disposed in said plane on the inside of said first current probe between it and said second current probe, and in which said first secondary voltage probe is transversely disposed in said plane on the side of said first current probe away from said first primary voltage probe.

3. Apparatus according to claim 2 in which said first primary voltage probe and said first secondary voltage probe are both located on said dipole centerline.

4. Apparatus according to claim 3 in which said first primary voltage probe is spaced by substantially the distances s and 2s from, respectively, said first current probe and said second current probe, and in which said first secondary voltage probe is spaced by substantially the distance 3s from said first current probe.

5. Apparatus according to claim 1 further comprising:
signal generating means electrically coupled to said primary voltage probes and said secondary voltage probe and responsive to flow of current between said current probes through said body to produce first and second signals respectively representative of first and second non-zero voltage differentials existing in said body among the points of contact therewith of said primary voltage probes and said secondary voltage probe, said first and second voltage differentials being produced respectively by flows of current in different distributed current paths through said body, comparator means responsive to said first and second signals to derive from them a third signal which is a function of said first and second voltage differentials, and means responsive to said third signal to produce an output comprising information about such body.

6. Apparatus according to claim 5 in which said comparator means comprises subtractor means and said third signal is a function of a difference between said first and second voltage differentials.

7. Apparatus according to claim 5 in which said comparator means comprises divisor means and said third signal is a function of a quotient of such first and second voltage differentials.

8. Apparatus according to claim 1 further comprising a second secondary voltage probe mounted by, and projecting axially forward from said end of, said holder and adapted to contact said body concurrently with such first secondary voltage probe, such second secondary voltage probe corresponding to such second current probe and being disposed in such plane substantially on said second loop at a position thereon substantially displaced around such loop from the location of said second primary voltage probe on such loop.

9. Apparatus according to claim 8 in which said first and second primary voltage probes are both disposed in said plane transversely on the inside of such two current probes so each is between such current probes, and in which said first and second secondary voltage probes are disposed in said plane traversely outside of such first and second current probes.

10. Apparatus according to claim 9 in which such primary voltage probes and such secondary voltage probes are all disposed on said dipole centerline.

11. Apparatus according to claim 10 in which each of said primary voltage probes is displaced by the distances s and 2s from, respectively, its corresponding nearer current probe and the other farther current probe, and in which said first and second secondary voltage probes are each displaced by the distance 3s from the current probe corresponding thereto.

12. Apparatus according to claim 8 further comprising a first signal unit electrically coupled to said primary voltage probes and responsive to flow of current between said current probes through said body and a consequent voltage differential produced between said primary voltage probes to generate a first signal as a function of such voltage differential, a second signal unit electrically coupled to said secondary voltage probes and responsive to such current and a consequent voltage differential produced between said secondary voltage probes to generate a second signal as a function of such latter voltage differential, a comparator unit responsive to such two signals to derive from them a third signal as a function of the respective values of said first and second signals, and means responsive to said third signal to provide an output comprising information about such body.

13. Apparatus according to claim 8 in which each contour in said set of equipotential contours surrounding on said physical sheet the point of contact therewith of the one of said current probes corresponding to said set is a curve which is closed upon itself and is the locus of all points on the sheet separated approximately by the distances $yr_1$ and $yr_2$ from, respectively, such corresponding current probe and the other current probe, y is a variable, $r_1$ and $r_2$ are the approximate distances of the point of intersection of such curve and such dipole centerline from, respectively, such corresponding current probe and such other current probe, $r_1$ is greater than zero and less than $r_2$ and the ratio $r_1/r_2$ remains approximately constant.

14. Apparatus according to claim 13, in which said curve is a circle having approximately a radius R equal to $(r_2 r_1 / r_2 - r_1)$ and having a center disposed on said dipole centerline on the side of the corresponding current probe away from said point of intersection to be spaced from such current probe by the approximate distance $R - r_1$.

15. A device for performing evaluations of electroconductive bodies comprising:
a probe holder comprising:
a probe mounting head having a front end and a longitudinal axis and extending at said end transversely to either side of said axis, a pair of current probes mounted by, and projecting axially forward from said end of, said head, said current probes being separated by a transverse gap and being disposed on opposite sides of said axis on a transverse dipole centerline passing through such probes and axis, a pair of primary voltage probes mounted by, and projecting axially forward from said end of, said head and disposed transversely between said current probes on opposite sides of said axis, and at least one secondary voltage probe mounted by, and projecting axially forward from said end of, said head and disposed transversely outward of and adjacent to one of said current probes to the side of such probe away from said gap.

16. A device according to claim 15 in which said one secondary voltage probe is the first of a pair of such secondary voltage probes of which the second is mounted by, and axially projects forward from said end of, said head, and is disposed transversely outward of and adjacent to the other of said current probes to the said of such other probe away from said gap.

17. A device according to claim 16 in which the two probes in each such pair of current probes, primary voltage probes and secondary voltage probes is on substantially on said line and on opposite sides of said axis and is equidistantly spaced therefrom.

18. A device according to claim 17 in which such primary voltage probes, current probes and secondary voltage probes are respectively spaced from each other by the respective distances s, 3s, and 9s.

19. Apparatus for performing evaluations of electroconductive bodies comprising:
a pair of spaced current probes operable for that purpose to contact the exterior surface of such an electroconductive body and to pass therethrough a flow of current productive on such surface of two sets of equipotential contours respectively corresponding to such two current probes, the contours of each set being closed curves each surrounding the point of contact with such surface of the corresponding current probe, at least first, second and third voltage probes operable to contact said surface at respective locations spaced from each other and from said current probes, the points of contact with such surface of said first and second voltage probes being located on first and second of said contours respectively corresponding to one and the other such two current probes, and the point of contact with such surface of said third voltage probe being disposed substantially at a position on such first contour which is substantially displaced around that contour from the location thereon of such first voltage probe, signal generating means electrically coupled to said three voltage probes and responsive to said current flow and consequent voltages sensed by said voltage probes to produce two signals as a function of two substantially non-zero voltage differentials existing among such three voltage probes, comparator means responsive to such two signals to derive from them a resultant signal as a function of such two voltage differentials, and output means responsive to said resultant signal to provide an output comprising information about such body.

20. Apparatus according to claim 19 further comprising a bias signal source adapted to provide a bias signal of adjustably set selected value, said source being operable to render said resultant signal a function of said set value as well as said two voltage differentials.

21. Apparatus according to claim 19 further comprising validity checking means responsive to the exceeding of a predetermined limit by at least one voltage among the group of voltages consisting of the voltages sensed on said surface by said voltage probes in and by the differentials between such sensed voltages to provide an indication that said output from said output means is spurious.

22. A method of evaluating an electroconductive body comprising:

producing a flow of current through such body between first and second points disposed on the exterior surface of such body in spaced relation from each other, such current being productive on such surface of two sets of equipotential contours respectively surrounding said first and second points and respectively corresponding thereto, the contours of each such set being closed curves surrounding the corresponding one of said points, sensing voltages developed by said current on such surface at least three locations spaced from each other and said points, a first and a second of said locations being on, respectively, first and second different equipotential contours respectively surrounding said first and second points, and the third of such locations being substantially at a position on said first contour displaced substantially around it from said first location thereon, deriving from said sensed voltages first and second signals as a function of the values of two voltage differentials existing between, respectively, said first and second locations and said third and second locations, deriving from said first and second signals a third signal as a function of such voltage differentials, and deriving from said third signal an output comprising information about such body.

23. A method according to claim 22 in which said electroconductive body is a mechanical part, and in which said output is indicative of a resistive condition produced in such part by a localized anomaly in the resistivity of such part.

24. A method according to claim 22 further comprising sensing the voltage produced on such surface by such current at a fourth location substantially at a position on said second equipotential contour displaced substantially around such second contour from said second location thereon, and deriving said second signal from the voltages actually sensed at, respectively, said third and said fourth locations so as to be a function of the voltage differential between such two voltages.

25. A method according to claim 22 in which said third signal is a function of a difference between said two voltage differentials.

26. A method according to claim 22 in which said third signal is a function of a quotient of said two voltage differentials.

27. A method according to claim 22 further comprising producing a bias signal having a set value to which such signal has been adjusted, and deriving said third signal in part from said bias signal to render such third signal a function of said set value as well as of such voltage differentials.

28. A method according to claim 22 further comprising comparing to a predetermined limit at least one voltage among the group of voltages consisting of such sensed voltages and the differentials between such sensed voltages, and providing, when such voltage exceeds such limit, an indication that said output is spurious.

* * * * *